Figure 1:
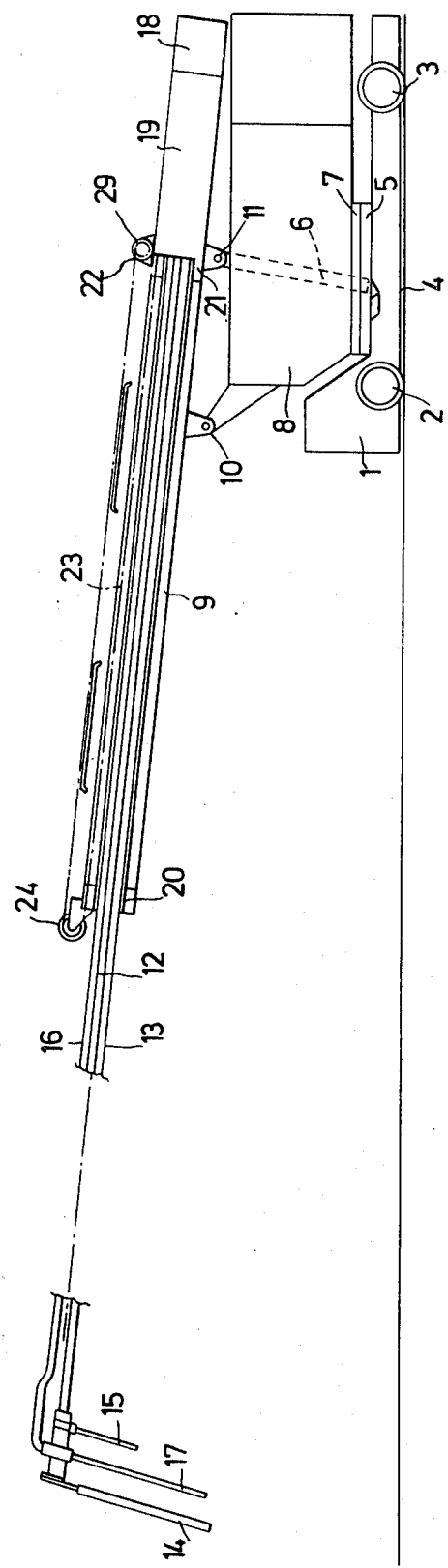

United States Patent [19]

Nautet et al.

[11] 4,003,261

[45] Jan. 18, 1977

[54] APPARATUS FOR TESTING MOLTEN METAL

[75] Inventors: Jean Adolphe Nautet, Liege; Philippe Felix Catoul, Horion-Hozemont, both of Belgium

[73] Assignee: Centre de Recherches Metallurgigues-Centrum voor Research in de Metallurgie, Brussels, Belgium

[22] Filed: Mar. 3, 1976

[21] Appl. No.: 663,553

[30] Foreign Application Priority Data

Mar. 7, 1975 Belgium .............................. 826455

[52] U.S. Cl. .............................. 73/423 R; 73/DIG. 9
[51] Int. Cl.$^2$ .......................................... G01N 1/12
[58] Field of Search ......... 73/423 R, 423 A, DIG. 9

[56] References Cited

UNITED STATES PATENTS

| 3,638,500 | 2/1972 | Wetzel et al. | 73/423 A |
| 3,916,693 | 11/1975 | Hancart et al. | 73/423 R |

Primary Examiner—S. Clement Swisher
Attorney, Agent, or Firm—Holman & Stern

[57] ABSTRACT

A measuring or sampling probe is to be lowered to a desired depth in molten metal. The probe is mounted on a tiltable elongate probe-carrier which can be lowered and raised. The probe-carrier is telescopic, its length being adjustable between given limits.

7 Claims, 3 Drawing Figures

APPARATUS FOR TESTING MOLTEN METAL

This invention relates to apparatus for testing molten metal by lowering a measuring or sampling probe into the molten metal, for example contained in a converter, a ladle, a pouring channel or an ingot mould.

The following description refers specifically to a probe for taking samples of molten steel, but this is by way of example only, and is not to be construed as limiting the scope of the invention.

A metallurgical process such as pig iron refining cannot be controlled correctly unless it is possible to know as accurately as possible the composition of the metal being processed, at the right moments. In order to take maximum advantage of information derived from knowledge of the metal composition at a given moment (for example, when the converter has just been turned down), it is necessary for the sample, the method of sampling and the method of analysis to satisfy certain quality criteria.

Particularly as far as the sample is concerned, a number of criteria are in use for judging its value; for instance: whether it is representative of the entire molten metal bath, its homogenity, its consistency, and the ease and duration of its preparation for analysis. The technique used for taking the sample has also to be taken into account, particularly as regards its simplicity, duration and cost.

Extensive study has already been made in order to ensure the best possible observance of such conditions. It appears, however, that as far as taking of samples is concerned the conventional procedures are liable to cause errors, so that accuracy in methods of analysis often becomes illusive, for example for want of representativeness of the sample.

It will be understood that, whatever technique is adopted, the quality of the samples taken depends to a large extent on human factors, since minor differencies in a way in which the sampling probe is used may result in considerable variations in representativeness and/or homogeneity. The very severe conditions (heat radiation, fumes, danger, physical strength needed) in which samples are taken are such that different samplers will never comply in the same way with pre-determined conditions regarding, for example, duration of immersion and, above all, the depth to and the spot at which the sampling probe is immersed.

To remedy these inconveniences, U.S. Pat. No. 3,916,693 discloses apparatus by means of which it is possible, on the one hand, to completely and effectively remedy the inconveniences referred to above, and, on the other, to permit accurate control of the penetration depth of the probe into the molten metal, such depth being adjustable at will.

Such apparatus comprises: a probe-carrier, and automatic means arranged to successively permit immersion of the probe in the molten metal, stopping of the probe at a predetermined depth in the molten metal, holding of the probe at a predetermined depth in the molten metal for a predetermined time, and withdrawal of the probe from the molten metal, the whole being mounted on a support structure, such as a carriage. This apparatus thus eliminates human intervention in most of the steps of the sample-taking operation.

The present invention has the object of improving the efficiency of testing apparatus such as that described in U.S. Pat. No. 3,916,693.

The probe-carrier by means of which the sampling in question can be carried out currently comprises a probe-carrying rod whose dimensions are sufficient to permit immersion of a probe in a metallurgical vessel, such as a converter, in a lowered position. Such a rod is usually 5m to 7m long or more. It will be readily understood that such dimensions, although indispensable for performing the desired sample-taking or measurement operations, could be too large in some circumstances if sufficient space is not available for moving or operating the apparatus in all locations within the working area.

According to the present improvement the probe-carrier is provided with a telescopic device which allows its length to be adjusted between two pre-determined limits and in particular to be shortened to a considerable extent, which results in much easier adjustments of the whole apparatus, which may adopt much smaller overall dimensions at times.

Furthermore, the support structure and all its equipment may be easily installed in works having a relatively small free space at the locations where samples (or measurements) are to be taken and where samples (or measurements) could not be taken by using a probe-carrying rod of fixed length.

In order to make its use easier, the support structure may be self-propelling, permitting displacement thereof on tyres or along a suitable track; it may comprise a turntable allowing rotating of the entire probe-carrier on the turntable, which in combination with the telescopic adjustability of the probe-carrier considerably facilitates utilisation of the apparatus.

Many ways exist of designing a telescopic device which may be adjusted by a driving device. However, if one is dealing with a probe which permits a sample of molten metal (for example steel, with or without slag) to be taken, and permits measurements of the temperature of the molten metal and of its oxygen activity to be made, the telescopic device must allow the passage of compressed-air pipes and electronic circuits needed for the such operations. Such pipes and circuits must be designed to compensate for the loosening occuring when the telescopic carrier is fully retracted, and to ensure without risk of failure their insertion into and withdrawing from the stationary part of the telescopic carrier during telescoping.

Figure 2:
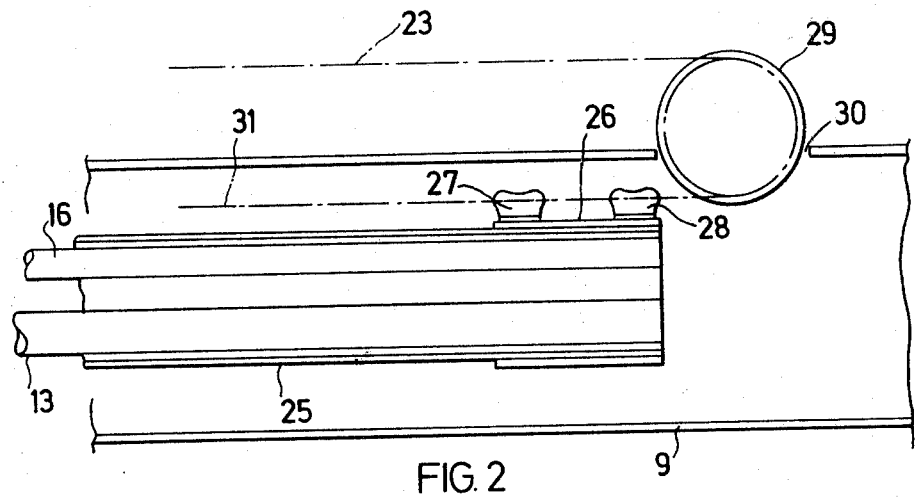
Figure 3:
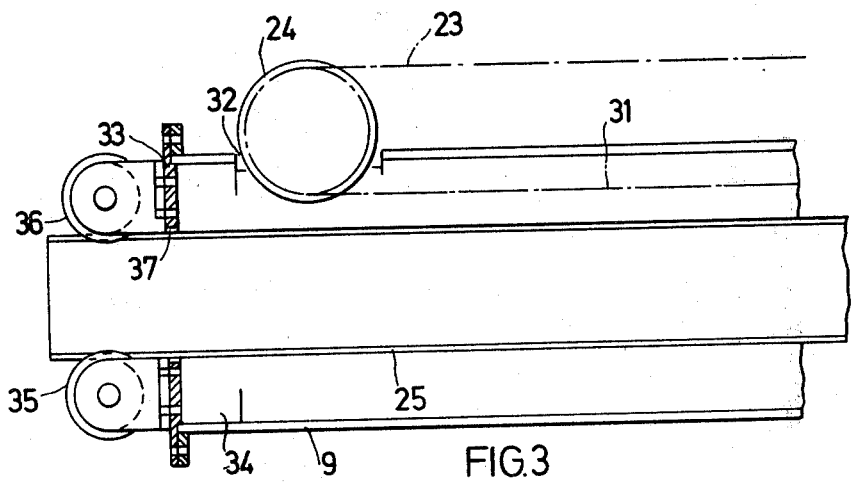

The invention will be described further, by way of example only, with reference to the accompanying drawings, in which:

FIG. 1 is a diagrammatic side elevation of apparatus for testing molten metal by lowering a sampling probe to a given depth in the molten metal; and FIGS. 2 and 3 are details of the rear part of the probe-carrier, in vertical section and on an enlarged scale.

The apparatus illustrated in the drawings mainly comprises; a movable carriage 1 with two groups of wheels 2 and 3, which roll along a track 4. The central and rear parts of the carriage 1 are lower than its front part; the central part carries a turntable plate 5 with vertical axis of rotation. A frame 8 is fixed on the upper face 7 of the turntable 5. The frame 8 carries a longitudinally-fixed rear part 9 of a probe-carrier by means of a fixed horizontal supporting shaft 10 and a movable horizontal supporting shaft 11 which is displaceable, in an almost vertical direction, by a jack mechanism 6 carried by the frame 8. Such displacement causes tilting of the probe-carrier about the fixed shaft 10. During tilting by extension of the jack mechanism 6, the remote end of the probe-carrier is lowered so as to immerse probes 14 and 17 to a suitable depth in the molten metal.

The elongate probe-carrier is telescopic and comprises the non-sliding rear part 9 and a sliding front part 12 substantially constituted by two parallel pipes 13, 16. The pipe 13 is designed to support a sampling probe 14 for taking a sample of molten metal and a cardboard tube 15 arranged to stop automatically the descent of the probe-carrier. The pipe 16 carries a measuring probe 17 for measuring the temperature and the oxygen activity of the molten metal. Behind the rear part 9 a ballast tank 18 acts as a counterweight for the probe-carrier and a box 19 contains connections and compensating lengths of the electric circuits and the pneumatic systems which connect the tube 15 and the probe 17 to measuring devices (not shown) by passing through the pipes 13 and 16 and the hollow rear part 9. The pipes 13 and 16 are caused to slide through an opening 20 in the front end of the part 9 by a roller mounted carriage 21 which is moved longitudinally in one direction or the other by a driving device comprising a pneumatic motor 22, a winding line in the form of a chain 23, and a pulley 24.

FIG. 2 shows a portion of the fixed rear part 9 of the probe-carrier, and the rear end of the movable front part constituted by the pipes 13 and 16. These two pipes 13,16 are (at least for the length thereof which may be caused to slide into the part 9) housed in a tubular casing 25 which carries a plate 26, at its rear end, forming part of the roller carriage 21 (not shown in FIG. 2) and serving as a support-connection to two stirrups 27 and 28. A sprocket 29 is driven by the motor 22 (FIG. 1). The end of the chain 23 adjacent to the sprocket 29 is attached to the stirrup 28. The chain 23 engages with the sprocket wheel 29 and passes through a longitudinal slot 30 formed in the top of the hollow part 9.

FIG. 3 shows the front end of the non-sliding part 9 of the probe-carrier. It also illustrates the casing 25, and the chain 23, whose internal run 31 is fixed to the stirrup 27 (FIG. 2). The chain 23 passes round the pulley 24, and its upper run extends to the sprocket 29 and thereafter to the stirrup 28. The chain 23 passes through a slot 32 formed in the front end of the part 9 and designed to suitably position the pulley 24. The lower run of the chain 23, after passing round the pulley 24, extends to the stirrup 27.

The hollow part 9 is closed at its front end by a plate 33 acting as a stop for a limit abutment 34 and as a support for two rollers 35 and 36 arranged to guide the casing 25. The plate 33 has an opening 37 for the passage of the casing 25.

The ends of the pipes 13 and 16 adjacent the probes side are subject to most severe thermal stress during the sample-taking operations, and thus are liable to be deformed. To prevent or reduce deformation, the assembly of the two pipes 13 and 16 may, at least in its portion which is not designed to enter the fixed part 9, be provided with a stiffening device extending mainly in a vertical direction.

The operation of the apparatus is simple. While the part 9 is being arranged at the desired inclination by the jack mechanism 6 acting on the shaft 11, the sliding part constituted by the casing 25 containing pipes 13 and 16 rests in the interior of the part 9 and is supported by means of the roller carriage 21 at its rear end and by means of the roller 35 at its front end. The box 19 serves as a rear-limit stop. Starting of the motor 22 results in the rotation of the sprocket 29 so that the chain 23 is displaced parallel to the axis of the probe-carrier, the external run of the chain moving from the front backwards, whereas the internal run 31 of the chain moves towards the front of the part 9, thereby displacing the sliding part. Forward displacement of the sliding part may take place until the carriage 21 (FIG. 1) abuts against the limit stop 34 (FIG. 3). At this point, the casing 25 will be extended to a maximum extent from the rear part 9 and is maintained in the correct position only by the lower roller 35 and the upper rollers of the carriage 21. It will be noted that, when the probe-carrier is in a completely lowered position, stresses exerted by the molten metal on the probes, will reduce the effect of the weight of the probe-carrier so that forces exerted on the roller 35 will decrease, while those exerted on the roller 36 will increase.

Return movement is performed by reversing the motor 22, which results in a backward movement of the internal run 31 of the chain 23, and thus the backward displacement of the casing 25.

The above-described apparatus is only a non-limiting example, and has a number of characteristics which form preferred embodiments from the constructional viewpoint.

First of all, displacement of the front part of the probe-carrier in the rear part occurs by means of rollers, which result in the advantage of having very reduced friction both because of the small area of the surfaces in contact and because rolling is considerably smaller than the sliding friction. Furthermore, this embodiment permits compensation to a certain extent for the deformations of the telescopic device, with no risk of jamming. This advantage is due to the fact that the use of rollers implies a relatively large radial gap between the front and rear parts of the probe-carrier, thereby reducing the area of actual contact near the rollers and between the rollers. To reduce any risk of failure or stopping due to particularly severe operating conditions in which the rod is normally to operate, the front end of the fixed part of the probe-carrier is provided with a sheet-metal cap having a profiled opening so as to define a passage just right for the sliding movement of the casing 25. In this way, the probability that the rollers 35 and 36 become clogged is reduced to a considerable extent. The rollers 35 and 36 may advantageously be provided with a device for adjusting the distance between them. Moreover, the rear part of the probe-carrier has a portion (18, 19) which the front part cannot enter, not even in its fully inserted position. A space is thus provided in which any length-compensating members for the various flexible supply and detection devices of the probes can be easily mounted. Finally, the displacement of the front part is advantageously controlled by a pneumatic motor and a chain or cable, bearing in mind that the autonomy of operation of a device of this kind is very large and control by chain or cable reduces to a minimum the dimensions of the slots to be formed in the pipe constituting the external envelope of the rear part of the probe-carrier.

We claim:
1. In apparatus for testing molten metal by lowering a measuring or sampling probe to a desired depth in the molten metal, the apparatus comprising a probe, an elongate probe-carrier, a support structure on which the probe-carrier is tiltably mounted, and means for lowering and raising the probe-carrier: the improvement that the probe-carrier is telescopic, its length being adjustable between given limits.

2. The apparatus of claim 1, in which the telescopic probe-carrier comprises a rear part rigid with the support structure, and a movable front part, both parts being tubular, the front part running inside the rear part.

3. The apparatus of claim 2, in which the probe-carrier includes rollers interposed between the said front and rear parts.

4. The apparatus of claim 2, in which, when the probe-carrier is adjusted to its minimum length, the length of the front part which lies inside the rear part is shorter than the total length of the rear part.

5. The apparatus of claim 1, in which the probe-carrier has a front part and a rear part, the apparatus further comprising a motor mounted on one said part, and a winding line connected between the motor and the other said part, whereby the length of the probe-carrier is adjustable.

6. The apparatus of claim 5, in which the motor is a pneumatic motor.

7. The apparatus of claim 1, in which the support structure includes a turntable on which the probe-carrier is mounted.

* * * * *